(12) United States Patent
Manzo et al.

(10) Patent No.: US 9,085,569 B2
(45) Date of Patent: Jul. 21, 2015

(54) 1,2,4-OXADIAZOL DERIVATIVES, PROCESS FOR THEIR PREPARATION AND USE THEREOF AS INTERMEDIATES IN THE PREPARATION OF INDOLIC ALKALOIDS

(71) Applicant: CONSIGLIO NAZIONALE DELLE RICERCHE, Rome (IT)

(72) Inventors: Emiliano Manzo, Napoli (IT); Dario Pagano, Boscoreale (IT); Maria Letizia Ciavatta, Napoli (IT); Marianna Carbone, Pozzuoli (IT); Margherita Gavagnin, Mugnano di Napoli (IT)

(73) Assignee: Consiglio Nazionale delle Ricerche, Rome (RM) (IT)

( * ) Notice: Subject to any disclaimer, the term of this patent is extended or adjusted under 35 U.S.C. 154(b) by 0 days.

(21) Appl. No.: 14/386,267

(22) PCT Filed: Mar. 19, 2013

(86) PCT No.: PCT/IB2013/052163
§ 371 (c)(1),
(2) Date: Sep. 18, 2014

(87) PCT Pub. No.: WO2013/140331
PCT Pub. Date: Sep. 26, 2013

(65) Prior Publication Data
US 2015/0051405 A1    Feb. 19, 2015

(30) Foreign Application Priority Data

Mar. 19, 2012    (IT) .............................. MI2012A0422

(51) Int. Cl.
*C07D 413/06*    (2006.01)
*C07D 271/07*    (2006.01)

(52) U.S. Cl.
CPC ............ *C07D 413/06* (2013.01); *C07D 271/07* (2013.01)

(58) Field of Classification Search
CPC ..................................................... C07D 413/06
See application file for complete search history.

(56) References Cited

PUBLICATIONS

Brogan et al. ACS Chem. Neurosci. 2012, 3, 658-664.*
Lin et al. J. Org. Chem. 2012, 77, 4832-4836.*
M. Carbone, et al., Structure and Cytotoxicity of Phidianidines . . . , Organic Letters, vol. 13, pp. 2516-2519, 2011, XP002676713.

* cited by examiner

*Primary Examiner* — Matthew Coughlin
(74) *Attorney, Agent, or Firm* — Lucas & Mercanti, LLP

(57) ABSTRACT

The present invention relates in general terms to a variously substituted 1,2,4-oxadiazol derivative, a process for their preparation, and use thereof as an intermediate in the preparation of indolic alkaloids, including phidianidine B and A.

12 Claims, No Drawings

1,2,4-OXADIAZOL DERIVATIVES, PROCESS FOR THEIR PREPARATION AND USE THEREOF AS INTERMEDIATES IN THE PREPARATION OF INDOLIC ALKALOIDS

CROSS-REFERENCE TO RELATED APPLICATIONS

This application is a 371 of PCT/IB2013/052163, filed Mar. 19, 2013, which claims the benefit of Italian Patent Application No. MI2012A000422, filed Mar. 19, 2012.

FIELD OF THE INVENTION

The present invention relates in general terms to a variously substituted 1,2,4-oxadiazol derivative, a process for their preparation, and the use thereof as an intermediate in the preparation of indolic alkaloids, including phidianidine B and A.

BACKGROUND ART

Indolic alkaloids are among the natural compounds which comprise a vast series of derivatives, some of which show very interesting pharmacological activity and properties, especially as regards the treatment of tumours or neoplastic pathologies in general. In particular, among the indolic alkaloids with these properties, phidianidine B is a natural molecule recently isolated together with the brominated derivative, phidianidine A, from the opisthobranch mollusk Phidiana militaris (Carbone et al., Organic Letters, 2011, 13(10), 2516-2519), collected in the South China Sea.

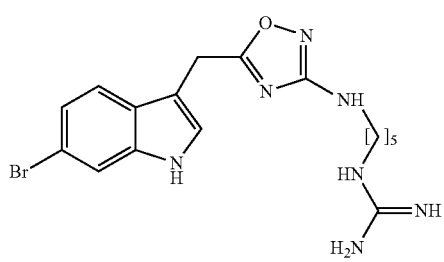

PHIADIANIDINE-A

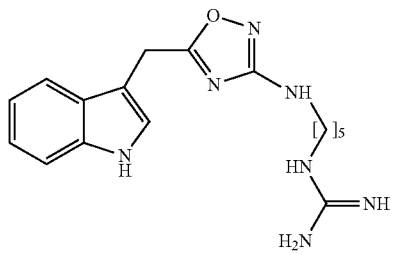

PHIDIANIDINE-B

Phidianidines are indolic alkaloids characterized by a 1,2,4-oxadiazol nucleus, a structural element never found in natural marine molecules, and they show an interesting, highly selective anti-proliferative activity on tumour cell lines at extremely low concentrations (nanomolar). In particular, phidianidine B has a high cytotoxic activity against the HeLa cell line (uterine cervix cancer).

Although the 1,2,4-oxadiazol nucleus is extremely rare in nature, there is enormous interest in synthesizing compounds containing this scaffold, since they are extensively used in medicinal chemistry programs as pro-drugs, being metabolically stable and bioavailable compounds. In the literature numerous syntheses of 1,2,4-oxadiazol nuclei have been described (e.g. Pace & Pierro, Org. Biomol. Chem., 2009, 7, 4337-4348 and cited references; Coté et al., Tetrahedron Lett., 2011, 52, 5750-5751; Nishiwaki et al., Org. Biomol. Chem., 2011, 9, 6750-6754; Sanchit et al., IJRAP, 2011, 2, 459-468).

The majority of the syntheses reported use two principal methods (Scheme A):
1) dipolar 1,3 cycloaddition of nitriles to nitrile oxides;
2) cyclization of amidoxime derivatives.

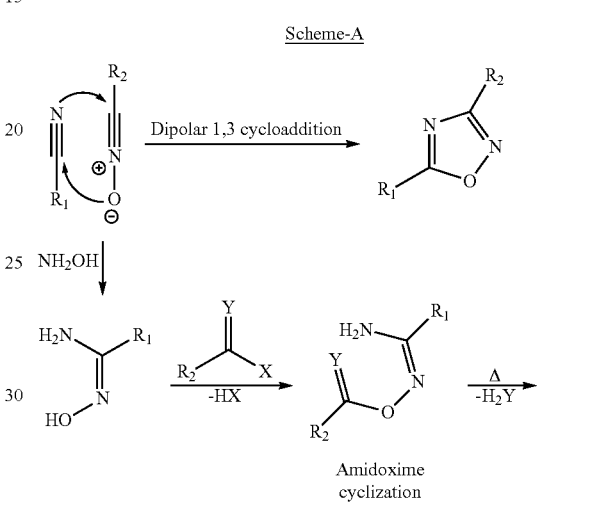

As said above, phidianidine A and B are isolated from a particular type of marine mollusk, which does not, however, enable large quantities of active ingredient to be obtained. It should be noted that the possibility of obtaining natural molecules with high pharmacological potential by chemical synthesis in the laboratory is without a doubt fundamental for gaining access to the high quantities of compound that are necessary for developing studies on biological activity.

The Applicant has found a new process for the preparation of a series of natural indolic alkaloid derivatives which, advantageously, enables the isolation of the products thereby obtained also in large quantities (in the order of tens of grams). The present process, in fact, comprises the preparation of a 1,2,4-oxadiazol key intermediate which, given its versatility, can be used to obtain a series of derivatives with potential antitumoural activity, including phidianidine A and B.

Moreover, the reaction for forming the 1,2,4-oxadiazol nucleus according to the present invention is carried out using an amidoxime, in particular a hydroxyguanidine, already containing the protected functional alkylamine group (4). In such a manner it is possible to avoid the problems connected to the subsequent introduction of the alkyl residue on a substrate containing two competing sites (indole NH and oxadiazole NH) as described in the literature.

SUMMARY OF THE INVENTION

The present invention relates to an indolic alkaloid derivative of formula (7), and pharmaceutically acceptable salts thereof:

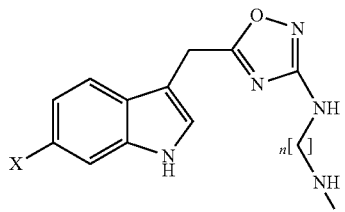

7 wherein:

R is selected between an N-protecting group or hydrogen;

X is selected from: hydrogen, chlorine, bromine, iodine and fluorine; and n is comprised between 1 and 8.

In a further aspect, the present invention relates to a composition containing a compound of formula (7) or pharmaceutically acceptable salts thereof, in a mixture with pharmaceutically acceptable carriers or additives.

The present invention also relates in general terms to a process for the preparation of indolic alkaloid derivatives, which comprises the steps of:

a) reacting a compound of formula (4):

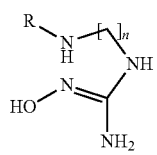

4 wherein:

n is comprised between 1 and 8; and

R is an N-protecting group;

with a compound of formula (5):

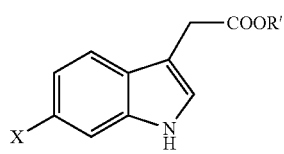

5 wherein:

R' is a straight or branched C1-C6 alkyl group, and

X is selected from: hydrogen, chlorine, bromine, iodine and fluorine;

in the presence of an inorganic base and a polar aprotic solvent to give a compound of formula (7a):

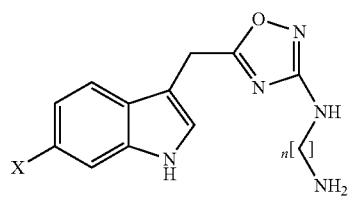

7a b) optionally removing the N-protecting group R to give a compound of formula (7b):

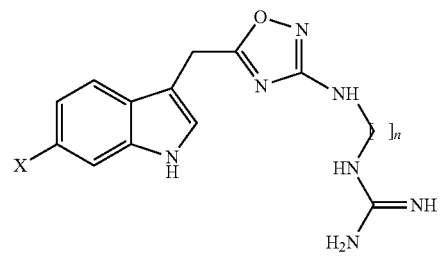

7b

In another aspect, the present invention relates to the use of a compound of formula (7) as an intermediate for the preparation of a compound of formula (8):

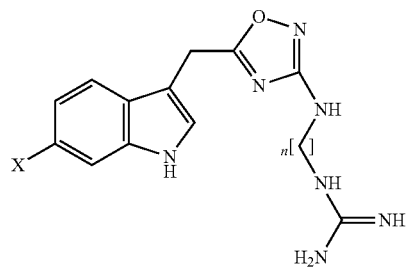

8 wherein n and X are as defined above.

In a further aspect, the present invention relates to a process for the preparation of a compound of formula (8) and pharmaceutically acceptable salts thereof:

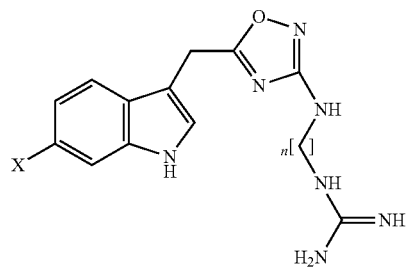

8 wherein:

n is comprised between 1 and 8;

X is selected from: hydrogen, chlorine, bromine, iodine and fluorine;

said process comprising the preparation of (7b) as above described being followed by functionalization with an activated guanylating agent, in the presence of an organic amine base.

DETAILED DESCRIPTION

The term straight or branched C1-C6 alkyl group comprises in its meaning a straight or branched hydrocarbon group comprising 1 to 6 carbon atoms, e.g.: methyl, ethyl, propyl, isopropyl, butyl, sec-butyl, ter-butyl, hexyl and the like.

The term N-protecting group relates to a protecting group bonded to a nitrogen atom which is used during the synthesis of the final compound to avoid secondary reactions on the nitrogen atom involved. Said protecting group is then typically removed to give the corresponding product in free form (see "Green's Protective Groups in Organic Synthesis", 4th edition, Peter G. M. Wuts).

As mentioned above, the present invention relates to a compound of the general formula (7) and pharmaceutically acceptable salts thereof, which can be conveniently isolated both in N-protected form (compound 7a) and in a free form (7b). According to a preferred aspect, the present invention relates to a compound of formula (7):

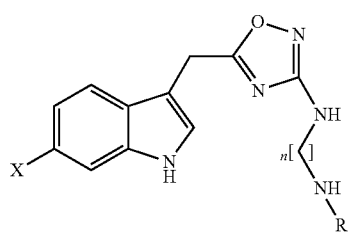

7 wherein:
R is hydrogen or an N-protecting group selected from: tert-butoxycarbonyl (BOC) and benzyloxycarbonyl (Cbz);
X is selected from: hydrogen, chlorine, bromine, iodine and fluorine; and
n is comprised between 1 and 8.

In a particularly preferred embodiment, in the compound of the general formula (7):
R is hydrogen;
X is selected from: hydrogen and bromine, and
n is comprised between 1 and 8.

In a particularly preferred embodiment, the present invention relates to a compound of formula (7) wherein:
R is hydrogen or BOC;
X is hydrogen; and
n is 5.

Equally preferred is a compound of formula (7) wherein:
R is hydrogen or BOC;
X is bromine; and
n is 5.

Salts of the amino form of the present compounds of formula (7) can be obtained by adding acids, according to methods known in the art, and can be obtained from both inorganic and organic acids. Examples of suitable organic acids include: maleic, malic, fumaric, ascorbic, succinic and aspartic acid and the like. The employable inorganic acids can instead be selected from the group of: hydrochloric, hydrobromic, sulphuric acid and the like. Therefore, in the present invention the term "pharmaceutically acceptable salts" of the compounds of the general formula (7) is meant to include any type of salt as defined above.

The present invention also relates to compounds of formula (7) which are isotopically marked, i.e. which contain one or more atoms having an atomic mass or atomic number different from the ones commonly known in nature. Examples of isotopes of atoms that can be incorporated in the present invention include, hydrogen, carbon, nitrogen, oxygen, fluorine, chlorine and iodine, such as: 3H, 11C, 14C, 18F, 123I and 125I.

As mentioned above, the present invention enables a derivative of formula (7) to be prepared and isolated by reacting a compound of formula (4) with an indolic derivative of formula (5).

To this end, the derivative (4) can be prepared according to scheme 1:

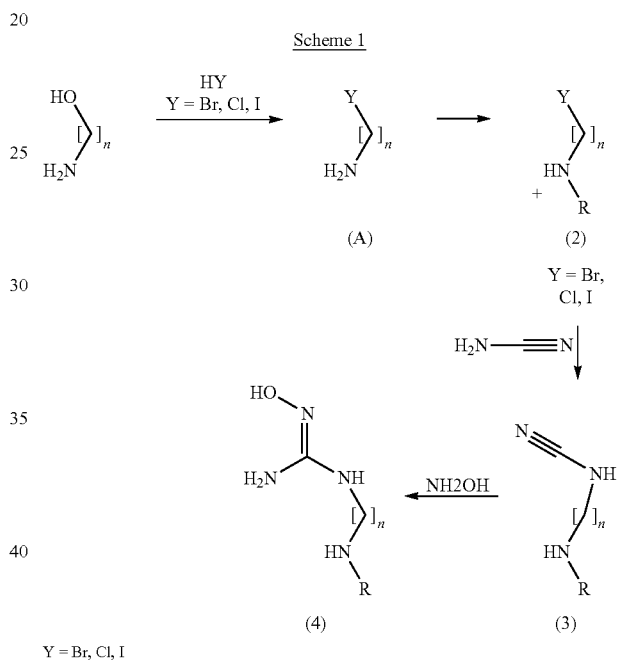

In particular, the starting amino alcohol, in which n is comprised between 1 and 8, is functionalized by halogenation, typically bromination, e.g. with hydrobromic acid, and subsequent protection of the amino nitrogen with a suitable protecting group R, so as to obtain the N-protected compound (2). The protecting group R for the amino nitrogen can be conveniently selected from among the protecting groups commonly used in organic chemistry, e.g.: tert-butoxycarbonyl (BOC), benzyloxycarbonyl (CBz), and the like (for general reference see "Green's Protective Groups in Organic Synthesis", 4th edition, Peter G. M. Wuts). Preferably, the protecting group is the tert-butoxycarbonyl group (BOC).

By substitution with cyanamide in the presence of an inorganic base, e.g. sodium amide, it is thus obtained the compound (3), which, via a subsequent reaction with hydroxylamine, leads to the product (4).

According to a particularly preferred embodiment, in the compound (4) the protecting group R is the tert-butoxycarbonyl (BOC) group and n is equal to 5. Equally preferred is an embodiment wherein R is the benzyloxycarbonyl (Cbz) group and n=5.

The indolic ester compound (5), on the other hand, can be prepared by esterification of the corresponding acid derivative according to the following scheme:

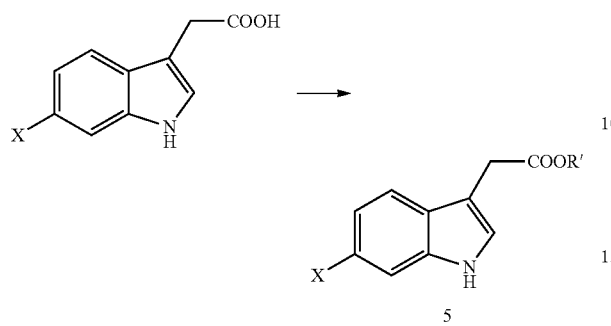

wherein:

R' is a straight or branched C1-C6 alkyl group selected from: methyl, ethyl, propyl, isopropyl, butyl, sec-butyl and the like, and X represents hydrogen or halogen, i.e. chlorine, bromine, fluorine or iodine.

Typically, the starting acid indolic compound undergoes an esterification reaction with an alcohol, in the presence of an acid, e.g. hydrochloric acid. Alcohols suitable for this purpose are selected from straight or branched C1-C6 alcohols, such as methanol, ethanol, propanol, isopropanol and the like. Preferably, the alcohol is methanol and the compound (5) is the methyl ester of the corresponding starting acid. Therefore, according to a particularly preferred embodiment, in the compound (5), R' is methyl and X is hydrogen. Equally preferred is an embodiment wherein in the compound (5), R' is methyl and X is bromine.

In accordance with the present invention, the aforesaid compounds (4) and (5) are reacted together, in the presence of a suitably selected inorganic base and organic solvent, to give a compound of the general formula (7) in N-protected form (7a), which can be deprotected, if necessary, to give the derivative (7b) according to scheme 2:

Scheme 2

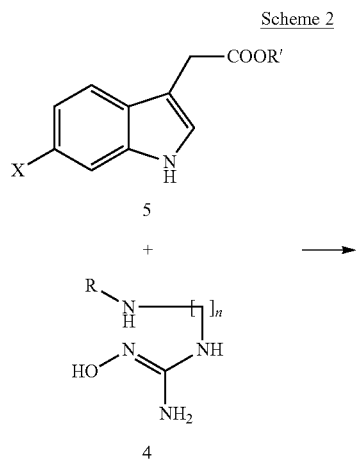

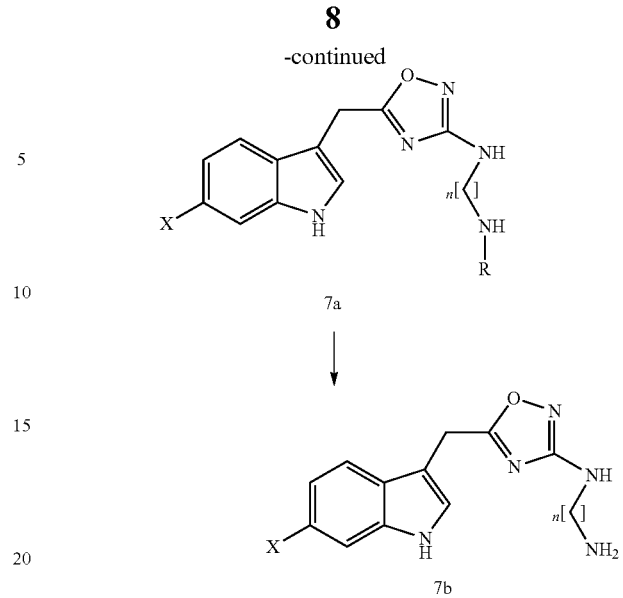

The inorganic base used for the reaction between (4) and (5) can be selected from inorganic hydrides, preferably alkali metal hydrides, e.g. KH, LiH and even more preferably NaH. The reaction solvent is an a polar aprotic solvent. Examples of the solvents that can be used are: dioxane, acetonitrile and tetrahydrofuran (THF), the latter being particularly preferred. According to a preferred embodiment, the compound (4) is reacted with the compound (5), in the presence of THF as the solvent and NaH as the base. Generally, the selected base is suspended in the selected polar aprotic solvent, and the indolic compound of formula (5), dissolved in a suitable solvent, is initially added to this suspension. The base is used in a molar excess comprised between 1.5 and 3 equivalents over (5) and comprised between 0.1 and 1 equivalents over (4).

Generally, the compound (5) is dissolved in the same solvent in which the base is suspended, e.g. THF. The mixture comprising the compound (5) and the base is then heated to a temperature above 35° C., more preferably to a temperature of at least 40° C., even more preferably to a temperature comprised between 50 and 60° C., so as to favour the solubilization of the reagents in the reaction environment. After a frame of time, generally comprised between 30 and 60 minutes, the compound (4), previously dissolved in a polar aprotic solvent, e.g. THF, is added to the reaction mixture containing (5), and the solution thus obtained is made to react, typically at the same reaction temperature at which the addition was made, for a variable amount of time which also depends on the quantities and experimental conditions used. By way of example, when the solvent is THF and the addition of (4) to the solution containing (5) and the base is made at a temperature of 50-60° C., according to a preferred embodiment, the reaction mixture is maintained at that temperature for a period of time comprised between 1 and 2 hours. On completion of the reaction, the mixture is divided between water and a non-polar organic solvent, e.g. ethyl acetate, and the organic phase, containing the N-protected compound (7a), is purified using known techniques, e.g. chromatographic purification, thus enabling the compound (7a) to be isolated in pure form and with good yields (greater than 50%).

The compound (7a) can then be subjected to an N-deprotection reaction by removing the protecting group R to give the compound of formula (7b). The reaction conditions for the deprotection will typically depend on the type of protecting group used. Therefore, in accordance with the known technique, in the case of protection with a BOC group, the compound (7a) is deprotected in an acid environment, e.g. in the presence of trifluoroacetic acid (TFA), in a non-polar organic solvent such as methylene chloride or the like.

Advantageously, the present process allows the preparation of a compound of formula (7b), corresponding to the compound of the aforesaid general formula (7) in a free form, i.e. in which R=hydrogen, with good overall yields (greater than 60%) and in a short period of time.

According to a further embodiment of the present invention, the N-protected compound (7a), preferably N-BOC protected, can also not be isolated from the reaction environment and be directly subjected to a deprotection reaction, thus enabling the compound (7b) to be obtained with a one-pot process according to scheme 3:

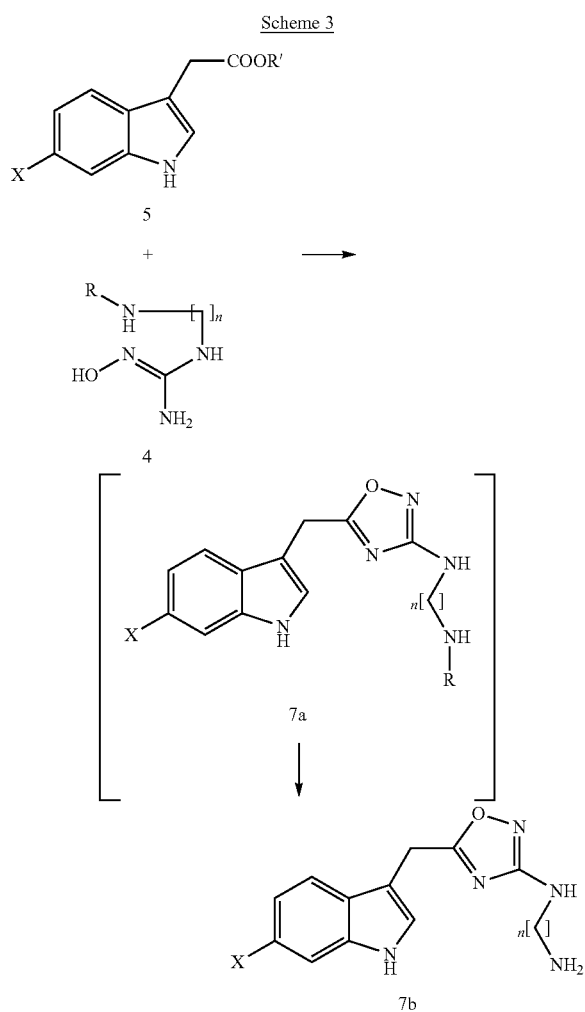

wherein n, X, R and R' are as defined above.

In this way, the present process will enable the compound of the general formula (7) to be obtained and isolated in a free form (i.e. the compound (7b)), useful as an intermediate in the preparation of indolic alkaloid derivatives, directly from the reaction of (4) with (5), in a single step and in a shorter reaction time.

Unless otherwise indicated, all of reagents and reactive agents are commercially available and easily obtainable by the person skilled in the art.

Advantageously, the present process enables the compound of the general formula (7) to be prepared and isolated both in a protected form (7a) and in a free form (7b), as described above, in good yields and in amounts in the order of tens of grams, thus permitting a possible industrial application, where large quantities of raw material are generally used. Moreover, the present process makes it possible to form the 1,2,4-oxadiazol nucleus, characteristic of the compounds of the invention, using an amidoxime bearing the protected alkylamine functional group, thus avoiding the subsequent introduction of said alkyl group on a reaction site otherwise containing two competing reaction sites, i.e. indole NH and oxadiazole NH.

A further advantage of the present invention is the fact that the compound of the general formula (7) can be further functionalized, leading to the formation of a series of final compounds of formula (8), e.g. structural analogues of phidianidine A and B, and thus potentially useful as cytotoxic agents in the treatment of tumours, in particular in the treatment of uterine cervix cancer.

The present compounds of formula (8):

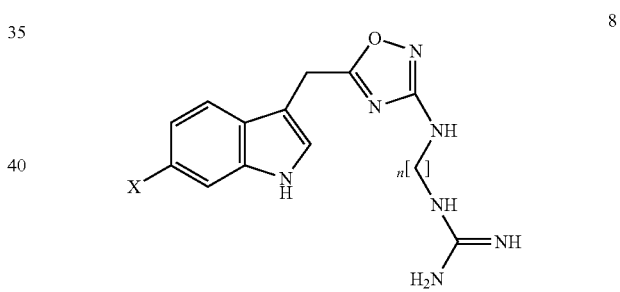

wherein:

n is comprised between 1 and 8;

X is selected from: hydrogen, chlorine, bromine, iodine and fluorine;

in fact show a high cytotoxicity, demonstrated by an interesting, highly selective anti-proliferative activity on tumour cell lines, also at extremely low concentrations, e.g. nanomolar concentrations.

Therefore, in a further aspect, the present invention relates to the use of a compound of formula (7) as previously obtained, as an intermediate in the preparation of a series of indolic alkaloid derivatives (8).

In one aspect thereof, the invention relates to a process for the preparation of indolic alkaloid derivatives (8) which comprises the process for the preparation of (7) in a free form (i.e. compound 7b), as described above, followed by selective functionalization of the terminal amino group, in the presence of an activated guanylating agent and an amine base:

Scheme 3

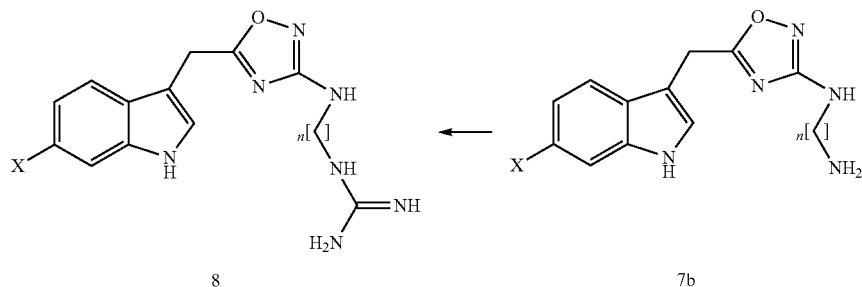

wherein X and n are as defined above.

The utilizable guanylating agent is preferably activated with diazole substituents, preferably alkyl substituted, even more preferably dialkyl substituted. In a particularly preferred embodiment, the activated guanylating agent is the compound 3,5-dimethyl-1-pyrazolyl formamidinium nitrate of formula:

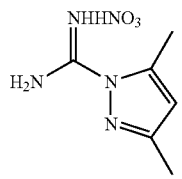

The amine base is an organic amine base selected from: triethylamine (TEA), diisopropylamine, and diisopropylethylamine (DIPEA). Preferably, the base is DIPEA. Practically, the amine base and the activated guanylating agent are added at room temperature (i.e. a temperature comprised between 15 and 35° C.), generally in equimolar amounts, to the compound (7) previously dissolved in a polar solvent, e.g. anhydrous N,N-dimethylformamide. The mixture is then made to react for a variable amount of time, generally longer than 6 hours. The solvent is then evaporated using known techniques, e.g. by evaporation under a stream of nitrogen or distillation, and the residue is purified, for example, using a chromatographic column so as to obtain the compound (8) in pure form and in good yields (>50%).

In a preferred embodiment, the present invention relates to the preparation of a derivative (8) wherein n is comprised between 4 and 8, more preferably wherein n is 5. In an equally preferred embodiment, the present invention relates to the preparation of a compound (8) wherein X is hydrogen or bromine.

According to a particularly preferred embodiment, the present invention relates to a process for the preparation of the indolic alkaloid compound of formula (8) from (7b) as previously discussed, wherein X is hydrogen and n=5, i.e. corresponding to the natural derivative phidianidine B of formula:

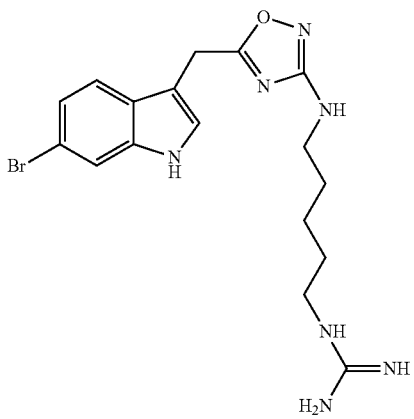 [SMILES: N=C(N)NCCCCCNc1noc(Cc2c[nH]c3cc(Br)ccc23)n1]

In a further preferred embodiment, the present invention relates to a process for the preparation of the indolic alkaloid compound of formula (8) from (7b) as previously discussed, wherein X is bromine and n=5, i.e. corresponding to the natural derivative phidianidine A of formula:

As exhaustively described, thanks to the present invention it is possible to obtain a series of indolic alkaloid derivatives of formula (8), including phidianidine A and B, in amounts that are useful and necessary for conducting experimental trials in order to test their potential pharmacological activity. In particular, the present invention enables a new, highly versatile key intermediate of formula (7) that can be synthesized and isolated either in an N-protected form (7a) or in a free form (7b), which can be variously substituted and thus used to obtain final compounds of formula (8) having potential antitumoural activity. The high yields and reproducibility of the synthetic steps, moreover, make the present process also suitable for a possible industrial application. To date, in fact, there are no known processes for preparing alkaloid derivatives such as phidianidine A and B which can be conveniently applied also on a large scale.

The invention will now be described by means of examples relating to the preparation of the derivative phidianidine B, with the aim of better illustrating the invention, without, however, limiting the scope thereof.

EXPERIMENTAL PART

Synthesis of Phidianidine B

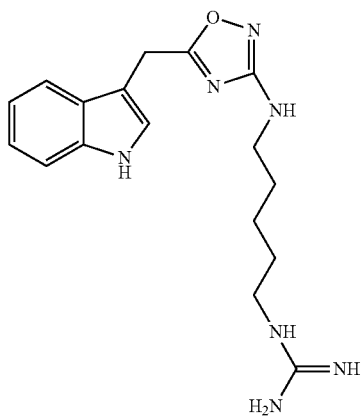 [SMILES: N=C(N)NCCCCCNc1noc(Cc2c[nH]c3ccccc23)n1]

Example 1

Preparation of Compound 5, Wherein R'=Methyl and X=H

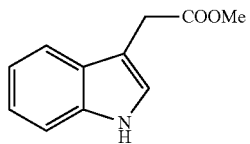 [SMILES: COC(=O)Cc1c[nH]c2ccccc12]

Indoleacetic acid (2.0 g, 0.0114 mol), purchased from Sigma-Aldrich, is dissolved in 25 mL of hydrochloric methanol 0.5 M and kept under stirring at room temperature for 2 h; after the reaction mixture has been evaporated and purified in a silica gel column with a gradient of chloroform/methanol eluents, compound 5 is obtained (2.1 g, 0.0112 mol, 98%); Rf (CHCl$_3$)=0.32; $^1$H-NMR (400 MHz, CD$_3$OD): δ=7.62 (1H, bd, J=7.4 Hz, H-7), 7.31 (1H, bd, J=7.4 Hz, H-4), 7.20 (1H, bt, J=7.4 Hz, H-6), 7.16 (1H, bt, J=7.4 Hz, H-5), 6.9 (1H, s, H-2), 3.69 (2H, s, H-8), 3.46 (3H, s, OCH$_3$); HRESIMS: m/z calcd for C$_{11}$H$_{11}$NO$_2$Na: 212.0687 [M+Na]$^+$; found: 212.0672.

Example 2

Preparation of Compound 4, wherein R=BOC and n=5

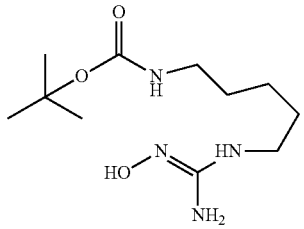 [SMILES: CC(C)(C)OC(=O)NCCCCCN/C(N)=N/O]

Sodium methoxide (97 mg, 0.0018 mol) is added to a solution of hydrochloric hydroxylamine (124 mg, 0.0018 mol) in 2.1 mL of anhydrous methanol, under argon at room temperature and under stirring for 1 h; a solution of compound 3 (0.408 g, 0.0018 mol) in anhydrous methanol (1 mL) is added to this mixture; the reaction mixture is kept under stirring at room temperature for 10 hours, heated to 53° C. for 7 hours and subsequently filtered to obtain compound 4 (0.442 g, 0.00170 mol, 96%); $^1$H-NMR (400 MHz, CD$_2$Cl$_2$): δ=3.24 (2H, bt, J=7.5 Hz, H$_2$-5), 3.06 (2H, m, H$_2$-1), 1.59 (2H, m, H$_2$-4), 1.52-1.33 (4H, m, H$_2$-2, H$_2$-3), 1.42-1.36 (9H, m, BOC-methyls); HRESIMS: m/z calcd for C$_{11}$H$_{25}$N$_4$O$_3$: 261.1927 [M+H]$^+$; found: 261.1939.

Example 3

Preparation of Compound 7a, wherein R=BOC and n=5 and X=H

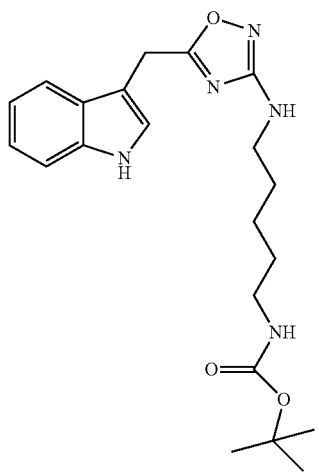 [SMILES: CC(C)(C)OC(=O)NCCCCCNc1noc(Cc2c[nH]c3ccccc23)n1]

Sodium hydride (50% in mineral oil, 645 mg, 0.013 mol) is suspended in 3 mL of anhydrous tetrahydrofuran; a solution of compound 4 in anhydrous tetrahydrofuran (3 mL) is added to this suspension; the mixture is heated to ° C. and after 40 minutes compound 5 (1.05 g, 0.0056 mol), in turn dissolved in tetrahydrofuran (3 mL), is added to it; after 1.5 hours under agitation at 52° C., the reaction mixture is divided between water and ethyl acetate; the organic phase is further purified in a silica gel column with a gradient of chloroform/methanol eluents to obtain compound 7a (1.34 g, 0.0029 mol, 51%); R$_f$ (CHCl$_3$/CH$_3$OH 9:1)=0.90; $^1$H-NMR (CD$_3$OD): δ=7.57

(1H, bd, J=7.7 Hz, H-7), 7.39 (1H, bd, J=7.7 Hz, H-4), 7.26 (1H, s, H-2), 7.15 (1H, bt, J=7.7 Hz, H-6), 7.07 (1H, bt, J=7.7 Hz, H-5), 4.26 (2H, s, $H_2$-8), 3.09 (2H, m, $H_2$-2"), 3.08 (2H, m, $H_2$-6"), 1.61 (2H, m, $H_2$-3"), 1.51-1.40 (4H, m, $H_2$-5", $H_2$-4"), 1.45-1.38 (9H, s, BOC-methyls); HRESIMS: m/z calcd for $C_{21}H_{30}N_5O_3$: 400.2349 [M+H]$^+$; found: 400.2363.

Example 4

Preparation of Compound 7b, wherein n=5 and X=H

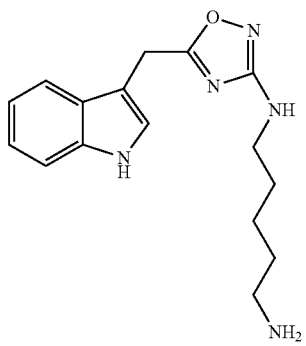 [SMILES: NCCCCCNc1noc(Cc2c[nH]c3ccccc23)n1]

Compound 7a (1.34 g, 0.0029 mol) is dissolved in 12 mL of a solution of trifluoroacetic acid and dichloromethane (1/1) and the mixture is kept under agitation at room temperature for one hour; subsequently, the reaction mixture is evaporated under a stream of nitrogen and purified in a silica gel column with a gradient of chloroform/methanol eluents to obtain compound 7b (0.57 g, 0.00174 mol, 60%); Rf (CHCl$_3$/CH$_3$OH 8:2)=0.25; $^1$H-NMR (400 MHz, CD$_3$OD): δ=7.57 (1H, bd, J=7.7 Hz, H-7), 7.39 (1H, bd, J=7.7 Hz, H-4), 7.24 (1H, s, H-2), 7.15 (1H, bt, J=7.7 Hz, H-6), 7.05 (1H, bt, J=7.7 Hz, H-5), 4.26 (2H, s, $H_2$-8), 3.16 (2H, bt, J=6.6 Hz, $H_2$-2"), 2.94 (2H, bt, J=7.2 Hz, $H_2$-6"), 1.73-1.62 (4H, m, $H_2$-3", $H_2$-5"), 1.47 (2H, m, $H_2$-4"); HRESIMS m/z calcd for $C_{16}H_{22}N_5O$: 300.1824 [M+H]$^+$; found: 300.1810.

Example 5

Preparation of Compound 8 Phidianidine B

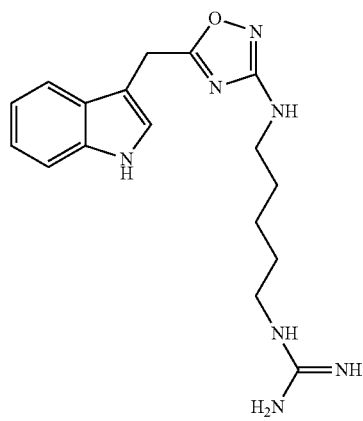 [SMILES: N=C(N)NCCCCCNc1noc(Cc2c[nH]c3ccccc23)n1]

3,5-dimethyl-1-pyrazolyl formamidinium nitrate (0.452 g, 0.00226 mol) and diisopropylethylamine (0.00226 mol) are added to a solution of compound 7b (0.57 g, 0.00174 mol) in 10 mL of anhydrous N,N-dimethylformamide; the mixture is kept under stirring at room temperature overnight; the reaction mixture is then evaporated under nitrogen and purified in a silica gel column with a gradient of chloroform/methanol eluents to obtain the final compound 8 (0.389 g, 0.00091 mol, 52%); R$_f$ (CHCl$_3$/CH$_3$OH 7:3)=0.51; $^1$H-NMR (400 MHz, CD$_3$OD): δ 7.57 (1H, bd, J=7.7 Hz, H-7), 7.39 (1H, bd, J=7.7 Hz, H-4), 7.26 (1H, s, H-2), 7.15 (1H, bt, J=7.7 Hz, H-6), 7.05 (1H, bt, J=7.7 Hz, H-5), 4.24 (2H, s, $H_2$-8), 3.17 (4H, m, $H_2$-2", $H_2$-6"), 1.72-1.62 (4H, m, $H_2$-3", $H_2$-5"), 1.46 (2H, m, $H_2$-4") (spectral data were identical to those of natural phidianidine-B); HRESIMS m/z calcd for $O_{17}H_{24}N_7O$: 342.2042 [M+H]$^+$; found: (342.2029).

Example 6

Preparation of Compound a, Wherein Y=Br and n=5

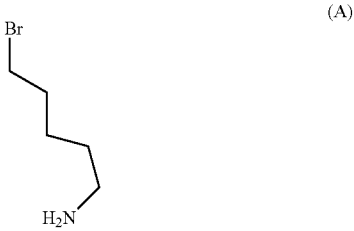

(A)

5-amino-1-pentanol (2.0 g, 0.0194 mol), purchased from Sigma-Aldrich, is dissolved in 20 mL of an aqueous solution of 48% hydrobromic acid; the mixture is stirred under reflux; after three hours the mixture is evaporated in a rotavapor to obtain a crystalline solid (4.37 g, 0.0178 mol, 92%); $^1$H-NMR (400 MHz, CD$_3$OD): δ 3.52 (2H, t, J=6.6 Hz, $H_2$-1), 3.01 (2H, bt, J=7.2 Hz, $H_2$-5), 1.95 (2H, m, methylene), 1.78 (2H, m, methylene), 1.60 (2H, m, methylene); $^{13}$C-NMR (75 MHz, CD$_3$OD): δ 40.5 (CH$_2$), 34.1 (CH$_2$), 33.1 (CH$_2$), 27.4 (CH$_2$), 25.8 (CH$_2$); HRESIMS m/z calcd for $C_5H_{13}BrN$: 166.0226 [M+H]$^+$; found: 166.0238.

Example 7

Preparation of Compound 2, wherein R=BOC, Y=Br and n=5

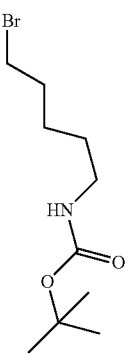

0.88 mL (0.0041 mol) of tert-butyloxycarbonyl and 53 mg (0.00041 mol) of iodine are added to compound A (1.0 g, 0.0041 mol); the mixture is kept under stirring for 4 hours at room temperature; subsequently, the reaction mixture is divided between a saturated aqueous solution of sodium carbonate and ethyl ether; the organic phase is purified in a silica gel column with a gradient of petroleum ether and ethyl ether to obtain compound 2 (0.76 g, 0.0029 mol, 70%); $^1$H-NMR (400 MHz, CD$_2$Cl$_2$): δ 3.42 (2H, t, J=6.6 Hz, H$_2$-1), 3.09 (2H, dt, J=6.1, 5.9 Hz, H$_2$-5), 1.88 (2H, m, methylene), 1.52-1.40 (4H, m, 2 methylene), 1.43-1.40 (9H, m, BOC-methyls); $^{13}$C-NMR (75 MHz, CD$_2$Cl$_2$)) 79.1 (C), 40.7 (CH$_2$), 34.3 (CH$_2$), 32.9 (CH$_2$), 28.5 (BOC—CH$_3$), 27.6 (CH$_2$), 25.8 (CH$_2$); HRESIMS m/z calcd for C$_{10}$H$_{21}$BrNO$_2$: 266.0752 [M+H]$^+$; found: 266.0768.

Example 8

Preparation of Compound 3, wherein R=BOC, and n=5

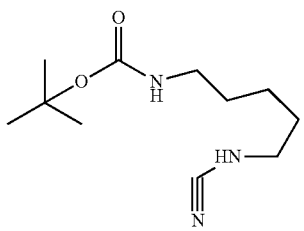 [SMILES: CC(C)(C)OC(=O)NCCCCCNC#N]

Cyanamide (80 mg, 0.0019 mol) is dissolved in 1 mL of anhydrous N,N-dimethylformamide at 0° C. and sodium amide (75 mg, 0.0019 mol) is added to this solution; the mixture is brought to room temperature and kept under stirring for 30 minutes; compound 2 (0.50 g, 0.0019 mol), in turn dissolved in 1 mL of anhydrous N,N-dimethylformamide, is added to this solution; after being kept under stirring overnight, the reaction mixture is evaporated under a stream of nitrogen and purified in a silica gel column with a gradient of petroleum ether-ethyl ether eluents to obtain compound 3 (0.408 g, 0.0018 mol, 94%); $^1$H-NMR (400 MHz, CD$_2$Cl$_2$): δ 3.07 (2H, m, H$_2$-5), 3.00 (2H, t, J=7.4 Hz, H$_2$-1), 1.62 (2H, m, H$_2$-2), 1.48 (2H, m, H$_2$-4), 1.45-1.39 (9H, m, BOC-methyls), 1.33 (2H, m, H2-3); HRESIMS m/z calcd for C$_{11}$H$_{22}$N$_3$O$_2$: 228.1712 [M+H]$^+$; found: 228.1700.

The invention claimed is:

1. A compound of formula (7) or pharmaceutically acceptable salts thereof:

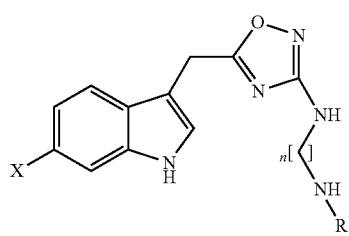

wherein:
R is hydrogen or an N-protecting group;
X is selected from: hydrogen, chlorine, bromine, iodine and fluorine; and
n is comprised from 1 to 8.

2. The compound according to claim 1, wherein R is hydrogen or a protecting group selected from: tert-butoxycarbonyl (BOC) and benzyloxycarbonyl (Cbz).

3. The compound according to claim 1, wherein:
R is hydrogen;
X is selected from: hydrogen, chlorine, bromine, iodine and fluorine; and
n is comprised between 1 and 8.

4. The compound according to claim 1, wherein:
R and X are both hydrogen; and
n is 5;
or
R is hydrogen;
X is bromine; and
n is 5.

5. A process for the preparation of indolic alkaloid derivatives, which comprises the steps of:
a) reacting a compound of formula (4):

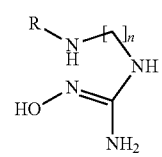

wherein:
n is comprised from 1 to 8; and
R is an N-protecting group;
with a compound of formula (5):

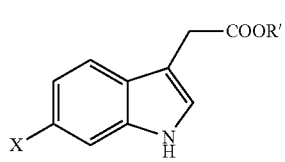

wherein:
R' is a straight or branched C1-C6 alkyl group, and
X is selected from: hydrogen, chlorine, bromine, iodine and fluorine;
in the presence of an inorganic base and a polar aprotic solvent to give a compound of formula (7a):

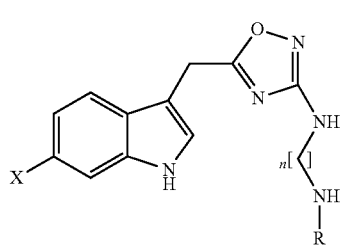

b) optionally removing the N-protecting group R to give a compound of formula (7b):

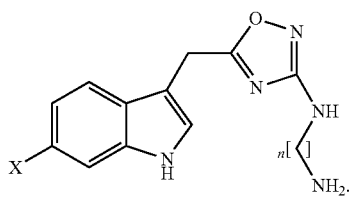

6. The process according to claim 5, wherein said inorganic base is an alkali metal hydride.

7. The process according to claim 5, wherein said polar aprotic solvent is selected from the group consisting of: dioxane, acetonitrile and tetrahydrofuran (THF).

8. A process for the preparation of a compound of formula (8):

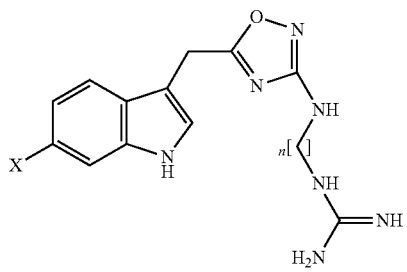

wherein:

n is comprised between 1 and 8;

X is selected from: hydrogen, chlorine, bromine, iodine and fluorine;

said process comprising the preparation of a compound of formula (7b) according to claim 5, followed by reaction with an activated guanylating agent, in the presence of an organic amine base.

9. The process according to claim 8, wherein said guanylating agent is activated with diazole substituents.

10. The process according to claim 9, wherein said activated guanylating agent is 3,5-dimethyl-1-pyrazolyl formamidinium nitrate of formula:

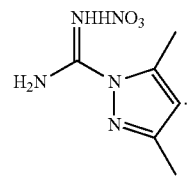

11. The process according to claim 6, wherein the alkali metal hydride is sodium hydride.

12. The process according to claim 9, wherein the guanylating agent is alkyl substituted.

* * * * *